US008133857B2

(12) United States Patent
Aikawa

(10) Patent No.: US 8,133,857 B2
(45) Date of Patent: Mar. 13, 2012

(54) NOTCH INHIBITION IN THE TREATMENT OF ATHEROSCLEROSIS

(75) Inventor: Masanori Aikawa, Chestnut Hill, MA (US)

(73) Assignee: The Brigham and Women's FHospital, Inc., Boston, MA (US)

(*) Notice: Subject to any disclaimer, the term of this patent is extended or adjusted under 35 U.S.C. 154(b) by 130 days.

(21) Appl. No.: 12/230,867

(22) PCT Filed: Mar. 2, 2007

(86) PCT No.: PCT/US2007/005267
§ 371 (c)(1), (2), (4) Date: Oct. 28, 2008

(87) PCT Pub. No.: WO2007/103114
PCT Pub. Date: Sep. 13, 2007

(65) Prior Publication Data
US 2009/0175849 A1 Jul. 9, 2009

Related U.S. Application Data

(60) Provisional application No. 60/779,445, filed on Mar. 7, 2006.

(51) Int. Cl.
A61K 31/00 (2006.01)
A61K 38/00 (2006.01)
A61K 39/00 (2006.01)
G01N 33/53 (2006.01)

(52) U.S. Cl. .............. 514/1; 514/1.9; 424/130.1; 435/4; 435/7.1

(58) Field of Classification Search .......................... None
See application file for complete search history.

(56) References Cited

U.S. PATENT DOCUMENTS

| | | | |
|---|---|---|---|
| 5,703,129 A | 12/1997 | Felsenstein et al. | |
| 6,448,229 B2 | 9/2002 | Teall | |
| 6,683,091 B2 | 1/2004 | Asberom et al. | |
| 6,703,221 B1 | 3/2004 | Chan et al. | |
| 6,756,511 B2 | 6/2004 | Castro Pineiro et al. | |
| 6,890,956 B2 | 5/2005 | Churcher et al. | |
| 6,967,196 B1 | 11/2005 | Smith et al. | |
| 6,984,626 B2 | 1/2006 | Nadin et al. | |
| 6,995,155 B2 | 2/2006 | Churcher et al. | |
| 7,161,006 B2 | 1/2007 | Crawforth et al. | |
| 7,183,303 B2 | 2/2007 | Castro Pineiro et al. | |
| 7,365,196 B2 | 4/2008 | Belanger et al. | |
| 2003/0180784 A1* | 9/2003 | McCarthy et al. ................ 435/6 |
| 2004/0102390 A1* | 5/2004 | Freier et al. ...................... 514/44 |
| 2005/0025751 A1 | 2/2005 | Bodmer et al. | |
| 2005/0026831 A1 | 2/2005 | Bodmer et al. | |
| 2005/0075320 A1 | 4/2005 | Nadin et al. | |
| 2005/0227973 A1 | 10/2005 | Brown et al. | |
| 2006/0004004 A1 | 1/2006 | Asberom et al. | |
| 2006/0009467 A1 | 1/2006 | Josien et al. | |
| 2006/0030694 A1 | 2/2006 | Kitajewski et al. | |
| 2006/0194315 A1* | 8/2006 | Condie et al. ................ 435/366 |
| 2007/0213266 A1* | 9/2007 | Gill et al. ........................ 514/12 |
| 2007/0213329 A1 | 9/2007 | Castro Pineiro et al. | |
| 2008/0206753 A1 | 8/2008 | Egan et al. | |
| 2009/0137470 A1 | 5/2009 | Stylianou | |
| 2009/0175849 A1 | 7/2009 | Aikawa | |
| 2009/0232813 A1 | 9/2009 | Beauchamp et al. | |

FOREIGN PATENT DOCUMENTS

| | | |
|---|---|---|
| WO | WO 02/081435 | 10/2002 |
| WO | WO 03/012441 A1 | 2/2003 |
| WO | WO 03/018543 A1 | 3/2003 |
| WO | WO 03/041735 A3 | 5/2003 |
| WO | WO 2005/008250 A1 | 1/2005 |
| WO | WO 2011/053822 A2 | 5/2011 |

OTHER PUBLICATIONS

High et al. The multifaceted role of Notch in cardiac development and disease. Nature Rev 9: 49-61, 2008.*
Clement et al. Notch3 and IL-1beta exert opposing effects on a vascular smooth muscle cell inflammatory pathway in which NF-kB drives crosstalk. J Cell Sci 120: 3352-3361, 2007.*
Rusanescu et al. Notch signaling in cardiovascular disease and calcification. Curr Cardiol Rev 4: 148-156, 2008.*
Aoyama et al. Gamma-secretase inhibitor reduces diet-induced atherosclerosis in apolipoprotein E-deficient mice. Biochem Biophys Res Comm 383: 216-221, 2009.*
Hofmann et al. Notch Signaling in Blood Vessels: Who is Talking to Whom About What? Circ Res 100: 1556-1568, 2007.*
Fung et al. Delta-like 4 induces Notch signaling in macrophages: Implications for inflammation. Circ Res 115: 2948-2956, 2007.*
Curry et al. Gamma secretase inhibitor blocks Notch activation and induces apoptosis in Kaposi's sarcoma tumor cells. Oncogene 24: 6333-6344, 2005.*
Bianchi et al. Physiology and Pathology of Notch Signalling System. J Cell Physiol 207: 300-308, 2006.*
Iso et al. Notch signaling in vascular development. Arterioscler Thromb Vasc Biol 23: 543-553, 2003.*
Fung et al. Induction of the notch pathway in activated human macrophages. Circulation 110(17): p. 274, abstract 1312, 2004.*
International Search Report for PCT/2007/05267 filed Mar. 2, 2007.
Written Opinion of the International Searching Authority for PCT/2007/05267 filed Mar. 2, 2007.
International Preliminary Report on Patentability for PCT/US2007/005267 filed Mar. 2, 2007.
Artavanis-Tsakonas, et al., "Notch Signaling: Cell Fate Control and Signal Integration in Development," *Science* 284:770-776 (Apr. 1999).

(Continued)

*Primary Examiner* — Bridget E Bunner
(74) *Attorney, Agent, or Firm* — Law Office of: Michael A. Sanzo, LLC

(57) ABSTRACT

The present invention is directed to methods of treating or preventing atherosclerosis and other cardiovascular diseases by administering agents that inhibit or modulate the NOTCH signaling pathway. In addition, the invention encompasses methods for assaying compounds for their ability to treat atherosclerosis based upon their effects on NOTCH signaling, and for measuring levels of amount, function, or activity of NOTCH pathway components in biological samples.

18 Claims, No Drawings

OTHER PUBLICATIONS

Brou, et al., "A Novel Proteolytic Cleavage Involved in Notch Signaling: The Role of the Disintegrin-Metalloprotease TACE," *Mol. Cell* 5:207-216 (Feb. 2000).

De Strooper, et al., "A Presenilin-1-Dependent γ-Secretase-Like Protease Mediates Release of Notch Intracellular Domain," *Nature* 398:518-522 (Apr. 1999).

Evin, et al., "A Synthetic Substrate Assay for the Gamma-Secretase of the β-A4 Amyloid of Alzheimer's Disease," *J. Pept. Sci.* 1(2):132-139 (1995).

Garg, et al., "Mutations in *NOTCH1* Cause Aortic Valve Disease," *Nature* 437:270-274 (Sep. 2005).

Hoke, et al., "In Vitro Gama-Secretase Cleavage of the Alzheimer's Amyloid Precursor Protein Correlates to a Subset of Presenlin Complexes and Is Inhibited by Zinc," *FEBS J.* 272:5544-5557 (2005).

Ikeuchi, et al., "The Notch Ligands, Deltal and Jagged2, Are Substrates for Presenilin-Dependent "γ-Secretase" Cleavage," *J. Biol. Chem.* 278(10):7751-7754 (Mar. 2003).

Itoh, et al., "Synergy and Antagonism Between Notch and BMP Receptor Signaling Pathways in Endothelial Cells," *EMBO J.* 23(3):541-551 (2004).

Lindner, et al., "Members of the *Jagged/Notch* Gene Families Are Expressed in Injured Arteries and Regulate Cell Phenotype via Alterations in Cell Matrix and Cell-Cell Interaction," *Am. J. Pathol.* 159(3):875-883 (Sep. 2003).

Mumm, et al., "A Ligand-Induced Extracellular Cleavage Regulates γ-Secretase-Like Proteolytic Activation of Notch1," *Mol. Cell* 5:197-206 (Feb. 2000).

Nobta, et al., "Critical Regulation of Bone Morphogenetic Protein-Induced Osteoblastic Differentiation by Deltal/Jagged1-Activated Notch1 Signaling," *J. Biol. Chem.* 280(16): 15842-15848 (Apr. 2005).

Peri, et al., "Development of Human Protein Reference Database as an Initial Platform for Approaching Systems Biology in Humans," *Genome Res.* 13(10):2363-2371 (2003).

Pinnix, et al., "A Novel γ-Secretase Assay Based on Detection of the Putative C-Terminal Fragment-γ of Amyloid β Protein Precursor," *J. Biol. Chem.* 276(1):481-487 (Jan. 2001).

Selkoe, et al., "Notch and Presenilin: Regulated Intrmembrane Proteolysis Links Development and Degenration," *Annu. Rev. Neurosci.* 26:565-597 (2003).

Sernee, et al., "Selecting Cells with Different Alsheimer's Disease γ-Secretase Activity Using FACS," *Eur. J. Biochem.* 270:495-506 (2003).

Shimizu, et al., "Physical Interaction of Delta1, Jagged1, and Jagged2 with Notch1 and Notch3 Receptors," *Biochem. Biophys. Res. Commun.* 276:385-389 (2000).

Shimizu, et al., "Mouse Jagged1 Physically Interacts with Notch2 and Other Notch Receptors," *J. Biol. Chem.* 274(46):32961-32969 (Nov. 1999).

Stockhausen, et al., "Effects of the Histone Deacetylase Inhibitor Valproic Acid on Notch Signaling in Human Neuroblastoma Cells," *Br. J. Cancer* 92:751-759 (2005).

Takizawa, et al., "Enhanced Gene Activation by Notch and BMP Signaling Cross-Talk," *Nucleic Acids Res.* 31(19):5723-5731 (2003).

Van ES, et al., "Notch/γ-Secretase Inhibition Turns Proliferative Cells in Intestinal Crypts and Adenomas into Goblet Cells," *Nature* 435:959-963 (Jun. 2005).

Wang, et al.,"μ Opiate Receptor: cDNA Cloning and Expression," *Proc. Natl. Acad. Sci. USA* 90:10230-10234 (Nov. 1993).

Weng, et al., "Activating Mutations of NOTCH1 in Human T Cell Acute Lymphoblastic Leukemia," *Science* 306:269-271 (2004).

Xu, et al., "Gamma-Secretase: Characterization and Implication for Alzheimer Disease Therapy," *Neurobiol. Aging* 23(6):1023-1030 (2002).

Abedin, et al., "Vascular Calcification Mechanisms and Clinical Ramifications," *Arterioscler. Thromb. Vasc. Biol.* 24:1161-1170 (2004).

Aikawa, et al., "The vulnerable atherosclerotic plaque Pathogenesis and therapeutic approach," *Cardiovasc. Pathol.* 13:125-138 (2004).

Aikawa, et al., "Arterial and Aortic Valve Calcification Abolished by Elastolytic Cathepsin S Deficiency in Chronic Renal Disease," *Circulation* 119:1785-1794 (2009).

Aster, et al., "Notch Signaling in Leukemia," *Annu. Rev. Pathol. Mech. Dis.* 3:587-613 (2008).

Chawla, "Control of Macrophage Activation and Function by PPARs," *Circ. Res.* 106:1559-1569 (2010).

Esposito, et al., "The metabolic syndrome and inflammation: association or causation?" *Nutr. Metab. Cardiovasc. Dis.* 14:228-232 (2004).

Fung, et al., "Delta-Like 4 Induces Notch Signaling in Macrophages: Implications for Inflammation," *Circulation* 115:2948-2956 (2007).

Gale, et al., "Haploinsufficiency of delta-like 4 ligand results in embryonic lethality due to major defects in arterial and vascular development," *Proc. Natl. Acad. Sci. USA* 101(45):15949-15954 (Nov. 2004).

Hotamisligil, "Inflammation and metabolic disorders," *Nature* 444:860-867 (Dec. 2006).

Iribarren, et al., "Metabolic Syndrome and Early-Onset Coronary Artery Disease," *J. Am. Coll. Cardiol.* 48(9):1800-1807 (2006).

Kanda, et al., "MCP-1 contributes to macrophage infiltration into adipose tissue, insulin resistance and hepatic steatosis in obesity," *J Clin. Invest.* 116(6):1494-1505 (Jun. 2006).

Liang, et al., "The Macrophage at the Crossroads of Insulin Resistance and Atherosclerosis," *Circ. Res.* 100:1546-1555 (2007).

Malik, et al., "Impact of the Metabolic Syndrome on Mortality From Coronary Heart Disease, Cardiovascular Disease, and All Causes in United States Adults," *Circulation* 110:1245-1250.

Radtke, et al., "Notch Signaling in the Immune System," *Immunity* 32:14-27 (Jan. 2010).

Shimizu, et al., "Notch Signaling Induces Osteogenic Differentiation and Mineralization of Vascular Smooth Muscle Cells," *Arterioscler. Thromb. Vasc. Biol.* 29:1104-1111 (2009).

Sutherland, et al., "The Metabolic Syndrome and Inflammation," *Metabolic Syndrome and Related Disorders* 2(2):82-104 (2004).

Swirski, et al., "Ly-6C$^{hi}$ monocytes dominate hypercholesterolemia-associated monocytosis and give rise to macrophages in atheromata," *J. Clin. Invest.* 117(1):195-205 (Jan. 2007).

Towler, et al., "Oxidation, Inflammation, and Aortic Valve Calcification," *J. Am. Coll. Cardiol.* 52(10):851-854 (2008).

Weng, et al., "Activating Mutations of NOTCH1 in Human T Cell Acute Lymphoblastic Leukemia," *Science* 306:269-271 (Oct. 2004).

Williams, et al., "Up-regulation of the Notch ligand Delta-like 4 inhibits VEGF-induced endothelial cell function," *Blood* 107(3):931-939 (Feb. 2006.

International Search Report for PCT/US2010/054798 filed Oct. 29, 2010.

Written Opinion of the International Searching Authority for PCT/US2010/054798 filed Oct. 29, 2010.

\* cited by examiner

NOTCH INHIBITION IN THE TREATMENT OF ATHEROSCLEROSIS

CROSS REFERENCE TO RELATED APPLICATIONS

The present application is U.S. national stage of international application PCT/US2007/005267, which had an international filing date of Mar. 2, 2007, and which was published in English under PCT Article 21(2) on Sep. 13, 2007. The international application claims priority to and the benefit of U.S. provisional application 60/779,445, filed on Mar. 7, 2006. This prior application is hereby incorporated by reference in its entirety.

CROSS REFERENCE TO RELATED APPLICATIONS

The present application claims priority to, and the benefit of, U.S. provisional application 60/779,445 filed on Mar. 7, 2006, the contents of which is hereby incorporated by reference in its entirety.

STATEMENT OF GOVERNMENT FUNDING

The United States Government has a paid-up license in this invention and the right in limited circumstances to require the patent owner to license others under reasonable terms as provided for by the terms of NIH Grant No. RO1 HL66086, awarded by the Department of Health and Human Services.

FIELD OF THE INVENTION

The present invention is directed to methods of treating or preventing atherosclerosis, its acute complications, and other cardiovascular diseases by administering agents that block or modulate the NOTCH signaling pathway. In addition, the invention encompasses assays for identifying therapeutic agents based upon their ability to block NOTCH signaling.

BACKGROUND OF THE INVENTION

The NOTCH signaling pathway has been identified as playing an important role in many diverse biological functions, including differentiation, and cellular proliferation (see U.S. Pat. No. 6,703,221). Mutations that increase NOTCH signaling have been associated with the development of leukemia and inhibitors of NOTCH are being studied for their potential use in the treatment of neurological diseases and cancer (Artavanis-Tsakonas, et al., *Science.* 284:770-776 (1999); Wang, et al., *Science* 306:269-271 (2004); Stockhausen, et al., *Br. J. Cancer* 92:751-759 (2005); Van Es, et al., *Nature* 435:959-963 (2005)).

The NOTCH pathway is activated by four different transmembrane receptor subtypes (designated as NOTCH-1-NOTCH-4) that rely upon regulated proteolysis. Expression patterns of NOTCH depend on cell type. Following ligand binding, the receptor undergoes sequential cleavage by metalloproteases of the ADAM family (Bru, et al., *Mol. Cell* 5:207-216 (2000); Mumm, et al., *Mol. Cell.* 5:197-206 (2000)) and the presenilin-dependent gamma-secretase (Selkoe, et al., *Annu. Rev. Neurosci.* 26:565-97 (2003); De Strooper, et al., *Nature* 398:518-522 (1999)). The final proteolytic cleavage step permits the intracellular domain of the NOTCH receptor to translocate to the cell nucleus where it interacts with transcription factors to induce target gene expression.

In the cell nucleus, the NOTCH intracellular domain undergoes ubiquitilation. Proteolytic processing of the NOTCH precursor protein by furin-protease and its trafficking to the cell membrane also determine turnover and availability of receptors, and, in turn, activation of this signaling pathway. Altered glycosylation of the Notch extracellular domain by Fringe protein family members may also modify efficiency of ligand binding.

As mentioned above, inhibitors of NOTCH, particularly gamma-secretase inhibitors, have received a great deal of attention as possible therapeutic agents for the treatment of neurological diseases (especially Alzheimer's disease) and cancer (especially leukemia). Additional therapeutic uses for agents that alter the NOTCH signaling pathway would be of clear interest to companies developing therapeutic agents in this area and to clinicians.

SUMMARY OF THE INVENTION

General Summary

The present invention is based upon experiments indicating that the NOTCH signaling pathway participates in macrophage activation and, as such, is a key contributor to the pathogenesis of inflammatory diseases such as atherosclerosis. Atherosclerotic plaques prone to acute thrombotic complications (e.g., myocardial infarctions, "heart attacks") contain many macrophages. Macrophage activation also contributes to other forms of vascular disease such as neointima formation after mechanical injury (e.g., restenosis following percutanous transluminal angioplasty or stent implantation), the failure of vein grafts used for coronary bypass surgery or hemodialysis shunts, and vasculitis. In addition, macrophage activation participates in the damage, remodeling, and impaired function of cardiac muscles following heart attacks; chronic heart failure; and brain damage following stroke.

As discussed herein, NOTCH signaling mediates macrophage activation. Evidence also suggests that the NOTCH pathway regulates osteogenic processes and thus calcification (Garg, et al., *Nature* 437:270-274 (2005); Nobuta et al., *J. Biol, Chem.* 280:15842-15848 (2005); Itoh et al., *EMBO J.* 23:542-551 (2004); Takizawa T et al., *Nucleic Acids Res* 31:5723-5732 (2003)). Therefore, agents that block or modulate NOTCH signaling in macrophages or other cell types either in vitro or in vivo should be useful in treating or preventing a variety of cardiovascular diseases. Assays for identifying agents, which block or modulate NOTCH signaling, will also be useful in identifying agents with potential use in the treatment of these conditions. In addition, measurement of levels of NOTCH pathway components in human tissues or blood samples may indicate the severity of atherosclerosis and other cardiovascular diseases, and thus predict future risks of acute complications and prognosis.

Specific Summary

In its first aspect, the invention is directed to a method of treating or preventing atherosclerosis in a patient by administering a therapeutically effective amount of a compound that inhibits or modulates the NOTCH signaling pathway. As used herein, the term "therapeutically effective amount" refers to a sufficient amount of a NOTCH inhibitor to prevent the development or growth of atherosclerotic plaques. The term "NOTCH inhibitor" refers to any agent capable of blocking NOTCH signaling. Mechanisms of action of such NOTCH inhibitors include, but are not limited to, inhibition of gamma-secretase and subsequent suppression of NOTCH receptor cleavage, inhibition of NOTCH trafficking to the cell membrane, suppression of expression or function of ligands and/or receptors, inhibition of ligand turnover, cleavage, and/or endocytosis, modification of NOTCH glycosylation, alteration of ubiquitilation of NOTCH components including the NOTCH intracellular domain, modification of expression and/or activity of co-factors or effectors (e.g., members of the MAML family, RBP-Jkappa/CBF-1), and alteration of differentiation/population of undifferentiated cells in bone marrow or circulating blood. Preferred inhibitors include receptor antagonists that block the binding of NOTCH ligands to receptors, RNA interfering agents for NOTCH components, blocking antibodies against NOTCH components, and, most preferably, gamma-secretase inhibitors. An alternative approach would be a systemic or local delivery of a DNA plasmid encoding a NOTCH component or a dominant negative form of such a component.

In another aspect, the invention is directed to a method for assaying a test compound to determine whether it has potential use in the treatment or prevention of atherosclerosis based upon its effect on the NOTCH signaling pathway. For example, test compounds may be incubated with gamma-secretase to determine whether proteolytic cleavage is prevented. Alternatively, receptor binding assays may be performed using test compounds in the presence of known ligands for NOTCH, e.g., Delta1 (Delta-like 1/Dll1), Delta4 (Delta-like 4/Dll4), Jagged 1 or Jagged 2 (see, e.g., Ikeuchi, et al., *J. Biol. Chem.* 278:7751-7754 (2003)) to determine the extent to which receptor binding is blocked. Compounds identified using these assays may undergo further evaluation in animal models to test their safety and potential clinical value.

Levels of expression, function, or activity of NOTCH components in a biological sample such as peripheral blood may indicate the severity of atherosclerotic changes and/or predict cardiovascular risk. Thus, the invention includes methods of determining whether a subject has or is likely to develop a cardiovascular disease by assaying a test biological sample derived from the subject for the amount of a NOTCH component that is present; comparing the results obtained with one or more control samples; and concluding that the subject is at increased risk of having or developing cardiovascular disease if the level of the amount, function, or activity of the NOTCH component is higher or lower in the test biological sample than in the control samples. Cardiovascular diseases that may be assessed in this manner include atherosclerosis and its acute effects (including heart attacks); restenosis after coronary intervention; failure of vein grafts for coronary bypass surgery or hemodialysis shunts; arterial calcification and vasculitis. The same procedure may also be used to determine the extent to which an atherosclerotic plaque has an inflammatory nature and is therefore likely to progress and cause more serious problems. Furthermore, this method may serve as a marker of inflammatory burden of other cardiovascular problems (e.g., damaged, remodeling, or dysfunctional cardiac muscles following acute myocardial infarction; chronic heart failure; valvular calcification and dysfunction; damaged brain following stroke) that predicts prognosis of these diseases.

The test biological sample may be blood, plasma, or serum (preferably derived from an area of the vascular close to where atherosclerotic plaques or similar lesions are known to exist or likely to form) or the biological sample may be cells or fluid derived directly from an atherosclerotic plaque or other cardiovascular tissues, e.g., a biopsy sample. The Notch component tested for may be a NOTCH receptor or a NOTCH ligand, particularly a ligand selected from the group consisting of: Delta1 (or Delta-like 1/Dll1), Delta3 (Delta-like 3/Dll3), Delta4 (Delta-like 4/Dll4), Jagged1, and Jagged2. Control samples may be selected using methods well known in the art and might constitute, for example, blood, serum plasma etc. from individuals known to be free of cardiovascular disease or from the population in general.

Finally, the involvement of the NOTCH pathway in differentiation, and cellular proliferation suggests that this pathway may be manipulated as a method of regenerating or engineering cardiovascular tissue. Thus, by modulating NOTCH signaling and/or altering the expression/function/activity of molecules relating to the NOTCH pathway, the growth or development of engineered cardiovascular tissues including, but not limited to, arteries, veins, heart valves, and myocardium may be promoted.

DETAILED DESCRIPTION OF THE INVENTION

A. Inhibitory Compounds

The present invention is directed to therapeutic methods in which an inhibitor of NOTCH signaling is administered to a patient to prevent the development or acute/chronic complications of cardiovascular diseases including atherosclerosis. Any of the NOTCH inhibitors, including gamma-secretase inhibitors, which have been described in the art may be used for this purpose. References describing such inhibitors and the way in which they can be made, purified, and used include: U.S. Pat. No. 5,703,129; U.S. Pat. No. 6,448,229; U.S. Pat. No. 6,683,091; U.S. Pat. No. 6,756,511; U.S. Pat. No. 6,890,956; U.S. Pat. No. 6,984,626; U.S. Pat. No. 6,995,155; WO 01/70677; WO 02/081435; WO 03/018543; WO 00/50391; WO 03/0422646; WO 03/041735; U.S. published application 2005-0227973; 2006-0030694; 2006-0004004; 2006-0009467; 2005-0261276; 2005-0143369; and 2005-0075320, all of which are hereby incorporated by reference.

Notably, expression and function of NOTCH pathway components depends strictly on context or cell type (Artavanis-Tsakonas, et al., *Science.* 284:770-776 (1999); Weng, et al., *Curr Opin Genet Dev* 14:48-54 (2004)). Therefore, in some contexts of cardiovascular diseases, induction of NOTCH signaling may prevent disease progression or complications.

B. Drug Formulation

The compounds described above will typically be administered to patients in a pharmaceutical composition comprising the compound along with a pharmaceutically acceptable carrier. The carrier may be any solvent, diluent, liquid or solid vehicle that is pharmaceutically acceptable and typically used in formulating drugs. Guidance concerning the making of pharmaceutical formulations can be obtained from standard works in the art (see, e.g., *Remington's Pharmaceutical Sciences,* 16$^{th}$ edition, E.W. Martin, Easton, Pa. (1980)). In addition, pharmaceutical compositions may contain any of the excipients that are commonly used in the art. Examples of carriers or excipients that may be present include, but are not limited to, sugars (e.g., lactose, glucose and sucrose); starches, such as corn starch or potato starch; cellulose and its derivatives (e.g., sodium carboxymethyl cellulose, ethyl cellulose, or cellulose acetate); malt; gelatin; talc; cocoa butter; oils (e.g., peanut oil, cottonseed oil, safflower oil, sesame oil, olive oil, corn oil, or soybean oil); glycols; buffering agents; saline; Ringer's solution; alcohols; lubricants; coloring agents; dispersing agents; coating agents; flavoring agents; preservatives; or antioxidants.

The invention is compatible with the delivery of compounds by any route known in the art, including peroral, internal, rectal, nasal, lingual, transdermal, intravenous, intra-arterial, intramuscular, intraperitoneal, intracutaneous and subcutaneous routes. The most preferred route is oral, especially using dosage forms such as tablets, capsules or solutions. In cases where a compound is susceptible to degradation in the stomach of a patient, it may be enterically coated or it may be administered parenterally.

It will be understood that pharmaceutical compositions may contain any pharmaceutically acceptable form of an inhibitory compound, i.e., any form which maintains therapeutic activity and which does not cause unacceptable adverse effects when administered. For example, a compound may be in the form of a pharmaceutically acceptable salt, ester or pro-drug.

Liquid dosage forms for oral administration include, but are not limited to, pharmaceutically acceptable emulsions, microemulsions, solutions, suspensions, syrups and elixirs. In addition to the active compounds, liquid dosage form may contain inert diluents commonly used in the art, such as, for example, water, or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, dimethyl formamide, oils, glycerol, alcohols, polyethylene glycols, and fatty acid esters.

Injectable preparations may be in the form of sterile, injectable aqueous or oleaginous suspensions, diluents or solvents that may be used may include 1,3-butanediol, water, Ringer's solution and isotonic saline solutions. In addition, oils or fatty acids may be present.

As mentioned previously, the most preferred dosage forms will be those for oral administration, particularly solid dosage forms such as capsules, tablets, pills, powders or granules. In these dosage forms, the active compound will typically be mixed with at least one inert, pharmaceutically acceptable excipient or carrier such as sodium citrate, or diacalcium phosphate and/or: fillers or extenders such as starches, lactose, sucrose, glucose, mannitol and silicic acid; binders such as, for example, carboxymethyl cellulose, alginates, gelatin, polyvinylpyrrolidinone, and acacia, humectants such as glycerol; disintegrating agents such as calcium carbonate, silicates or sodium carbonate; solution retarding agents such as paraffin; absorption accelerators such as quaternary ammonium compound; wetting agents such as cetyl alcohol or glycerol monostearate; absorbents such as kaolin; and lubricants, such as talc, magnesium stearate; sodium lauryl sulphate, etc. In addition, dosage forms may include buffering and flavoring agents.

Pharmaceutical compositions will typically be given to a patient in one or more unit dosage forms. A "unit dosage form" refers to a single drug administration entity, e.g., a single tablet, capsule or injection vial. The amount of inhibitory compound present should be at least the amount required to reduce the development or growth of atherosclerotic plaques when one or more unit dosage forms are administered to a patient. On a biological level, sufficient inhibitor should be present to reduce the NOTCH signaling pathway in the portions of the vasculature where plaques develop. For example, a sufficient amount of a gamma-secretase inhibitor may be included in unit dosage forms to reduce gamma-secretase activity by 20%, 40%, 60% or more. The exact dosages given and amount of inhibitor in unit dosage forms may be determined for individual compounds using methods that are well known in the art of pharmacology and may be further adjusted by physicians on a case-by-case basis based upon clinical considerations.

Alternative methods include local delivery of compounds including, but not limited to, gamma-secretase inhibitors, RNA interfering agents, and plasmid DNAs, to cardiovascular tissues surgically and/or via devices such as drug-eluting stents.

C. Treatment Methods

Subjects, particularly individuals at high risk of developing atherosclerosis, may be treated by administering one or more of the inhibitory compounds described above. As previously mentioned, the exact dosage will depend upon the particular compound being given and will be determined using procedures well known in the art, balancing toxicity and therapeutic efficacy. Compounds may also be given to test animals to study their effect on the development of atherosclerotic plaques. In these cases, dosages are limited only by toxicity. It should also be recognized that inhibitory compounds may be administered as the sole active agents in a dosage form, or they may be combined with other drugs to improve overall effectiveness.

D. Assays

Assays designed to identify compounds of potential use in atherosclerosis may involve any method known in the art for identifying compounds that block or modulate the NOTCH signaling pathway. The most common assays will be either enzymatic assays for inhibitors of gamma-secretase or assays to identify agents that interfere with receptor binding. In the former case, many different assays have been described in the art which may be utilized for examining the effect of a test compound on gamma-secretase activity. These include assays using radiolabeled substrates followed by HPLC or TLC analysis (see, e.g., Evin, et al., *J. Pept. Sci.* 1(2):132-139 (1995)); FACS assays (Sernee, et al., *Eur. J. Biochem.* 270: 495-506 (2003)); and other in vitro or in vivo assays (Pinnix, et al., *J. Biol. Chem.* 276:481-487 (2001); Xu, et al., *Neurobiol. Aging* 23(6):1023-1030 (2002); and Holke, et al., *FEBS J.* 272:5544 (2005)). All of these references are hereby incorporated by reference in their entirety. Commercially available assays such as the QTL Lightspeed assay (QTL Biosystems, Santa Fe, N. Mex.) may also be used.

Receptor binding assays may be adapted to identify compounds that interfere with the binding of NOTCH ligands have been described in the art and may be used in conjunction with the present invention (see, e.g., Shimizu, et al., *J. Biol. Chem.* 274(46):32961-32969 (1999); Shimizu, et al., *Biochem. Biohys. Res. Commun.* 276(1):385-389 (2000), both of which are hereby incorporated by reference in their entirety). In general, receptor binding assays are performed using a source of NOTCH receptor together with one of the ligands that are known to bind to the receptor and with the compound being tested for binding activity. As a source of receptor, mammalian cells that have been transformed to recombinantly express NOTCH-1-NOTCH-4 may be used. The assay itself may be performed either with intact cells or with membranes prepared from the cells (see, e.g., Wang, et al., *Proc. Natl. Acad. Sci. USA* 90:10230-10234 (1993)). The membranes or cells are incubated with one of the ligands for the NOTCH receptor (e.g., Delta1 (Delta-like 1/Dll1), Delta4 (Delta-like 4/Dll4), Jagged 1 or Jagged 2) and with a preparation of the compound being tested. After binding is complete, the receptor is separated from the solution containing ligand and test compound, e.g., by filtration, and the amount of binding that has occurred is determined. Preferably, the ligand used is detectably labeled with a radioisotope such as $^{125}$I, however, fluorescent chemiluminescent or enzymatic labels can also be used.

Nonspecific binding may be determined by carrying out the binding reaction in the presence of a large excess of unlabeled ligand. For example, labeled ligand may be incubated with receptor and test compound in the presence of a thousand-fold excess of unlabeled ligand. Nonspecific binding should typically be subtracted from total binding, i.e., binding in the absence of unlabeled ligand, to arrive at the specific binding for each sample tested. Other steps, such as washing, stirring, shaking, filtering and the like may be included in the assays as necessary. Typically, wash steps are included after the separation of membrane-bound ligand from ligand remaining in solution and prior to quantitation of the amount of ligand bound, e.g., by counting radioactive isotope. The specific binding obtained in the presence of test compound is compared with that obtained in the presence of labeled ligand alone to determine the extent to which the test compound has displaced receptor binding.

In performing binding assays, care must be taken to avoid artifacts which may make it appear that a test compound is interacting with the NOTCH receptor when, in fact, binding is being inhibited by some other mechanism. For example, the compound being tested should be in a buffer which does itself substantially inhibit the bind of ligand to the NOTCH receptor and should, preferably, be tested at several different concentrations. In addition, it is desirable that compounds identified as displacing the binding of ligand to receptor be reexamined in a concentration range sufficient to perform a Scatchard analysis of the results. This type of analysis is well known in the art and can be used for determining the affinity of a test compound for receptor (see, e.g., Ausubel, et al., *Curr. Protocols in Mol. Biol.*, 11.2.1-11.219 (1993); *Laboratory Techniques in Biochemistry and Molecular Biology*, Work, et al., NY (1978)). Computer programs may be used to help in the analysis of results (see, e.g., Munson, *Meth. Enzymol.* 92:543-577 (1983)).

The effects/actions of compounds can also be determined by other indicators of activated states of NOTCH signaling including, but not limited to, receptor cleavage and/or nuclear translocation, ligand cleavage and/or endocytosis, NOTCH trafficking to cell membrane, expression of ligands and/or receptors, ligand turnover, cleavage, and/or endocytosis, NOTCH glycosylation, ubiquitilation of NOTCH components including NOTCH intracellular domain, and expression and/or activity of co-factors or effectors (e.g., members of the MAML family, RBP-Jkappa/CBF-1), and differentiated state or population of undifferentiated cells in bone marrow or circulating blood.

E. Uses

The most obvious use of the present invention is in the administration of compounds to individuals to treat or prevent atherosclerosis progression or its acute complications (heart attacks) or other cardiovascular diseases. It should be appreciated however that treatments may also involve administering compounds to test animals by scientists interested in studying the biology of atherosclerotic plaque formation or other cardiovascular problems and in finding new ways to treat this and other cardiovascular diseases. Assays to determine the extent to which the NOTCH pathway is activated will also be of interest to scientists and clinicians interested in characterizing atherosclerotic plaques or other cardiovascular lesions as being inflammatory or non-inflammatory. Plaques in which cells have highly active NOTCH pathways are inflammatory and more prone to cause serious medical problems. Assays based upon NOTCH activity will be useful not only for individuals trying to identify therapeutic agents useful in treating atherosclerosis, but will also be of value in identifying agents for closely related conditions. Such compounds will be of particular value in the treatment of patients at high risk for the development of cardiovascular disease related to heart attacks and strokes.

EXAMPLES

Example 1

Delta-Like 4 Induces Notch Signaling in Macrophages: Implications in Inflammation The Notch family members (Notch 1-4) are large type I transmembrane receptors that undergo proteolytic processing by a furin-like convertase during transit to the cell surface (Logeat, et al., *Proc. Nat'l Acad. Sci. USA* 95:8108-8112 (1998)). Binding of a ligand—Delta-like 1 (Dll1), Delta-like 3 (Dll3), Delta-like 4 (Dll4), Jagged1, or Jagged2—triggers sequential receptor cleavage by ADAM-type metalloproteinases and gamma-secretase, resulting in the liberation and nuclear translocation of Notch intracellular domain (Notch$^{ICD}$) (Selkoe, et al. *Annu. Rev. Neurosci.* (2003)). Notch$^{ICD}$ association with the sequence-specific DNA-binding factor RBP-Jkappa/CBF-1 leads to the formation of a transcriptional activator complex that induces the transcription of Notch target genes. In the present example, data is presented showing that Dll4 expression increases in activated human macrophages, and that Dll4 binding induces pro-inflammatory responses. The findings suggest that the Dll4-Notch pathway participates in inflammatory states characterized by macrophage activation.

A. Methods

Cell Cultures

Human peripheral blood mononuclear cells were isolated by density gradient centrifugation and cultured in RPMI-1640 containing 5% human serum. In stimulation assays, confluent macrophages were treated with Ultra-pure LPS (InvivoGen), cytokines or minimally-modified LDL (mmLDL). Co-culture experiments employed a murine stromal cell line stably-transfected with a construct expressing human Dll4-GFP (MS5-Dll4) or GFP (MS5-GFP). Resuspended MS5 cells were overlain on human primary macrophages for the indicated duration, and rinsed thoroughly whereupon MS5 cells readily detached.

Reverse Transcription and Quantitative Polymerase Chain Reaction (qPCR)

TaqMan qPCR was performed on GeneAmp 5700 (Applied Biosystems). qPCR detection of human Dll4, Toll-like receptor 4 (TLR4), inducible nitric oxide synthase (iNOS), pentraxin 3 (PTX3) and Id1 was performed on iCycler (Bio-Rad). qPCR values were GAPDH-normalized and relative fold changes calculated by comparative threshold cycles ($C_T$) method, $2^{-deltaCT}$.

Transfection and RBP-Jkappa/CBF-1 Luciferase Reporter Assay 200 nM of small interfering RNA (siRNA) was applied to human macrophages using cationic lipid-mediated transfection. RBP-Jkappa/CBF-1 firefly-luciferase reporter construct and pRL-TK-*Renilla* luciferase were co-transferred into RAW264.7 cells using electroporation. RAW264.7 cells were then co-cultured with MS5-Dll4 or MS5-GFP cells for 48 h.

Luciferase activities were determined using the Dual-Luciferase Reporter Assay System (Promega).

Dll4.Fc Binding Assay

Dll4.Fc protein was generated using human full-length Dll4 cDNA subcloned into human IgG1 fusion protein vector, pEd.Fc. Dll4.Fc binding assays were performed using human macrophages. After blocking non-specific binding, 1 µg per reaction of Dll4.Fc or control Fc fragment pre-incubated with 0.5 µg biotinylated anti-human goat IgG at 15-20° C. was added for 30 min at 4° C. Streptavidin-PE (2.5 µg/ml) was then added for 45 min at 4° C.

Immunohistochemistry and Western Blotting

Immunohistochemistry employed fresh-frozen sections of discarded human carotid endarterectomy specimens, collected in accordance with a protocol approved by the IRB of the Brigham and Women's Hospital. For Western blotting, 80 µg of sample protein was loaded into each lane. Blots were stained with antibodies. Following incubation with HRP-tagged secondary antibodies, an ECL detection kit (Perkin Elmer) was used to reveal antibody binding.

Statistical Analysis

P values were obtained using the Mann-Whitney U test to compare GAPDH-normalized $C_T$ between control and treatment groups, or between day 0 and days 5, 7, or 10 samples. Individual relative fold changes were calculated using the equation $2^{-deltaCT}$ and expressed as mean relative fold changes ±standard error of the mean (S.E.M.). Pearson's correlation coefficient (R) with two-tailed test of significance was used to determine bivariate correlations.

B. Results

Notch3 Increases During Monocyte-Macrophage Differentiation

To explore the possible role of the Notch pathway in macrophages, we used real-time RT-PCR to examine the expression of Notch pathway components during the differentiation of human monocytes to macrophages in culture. Differentiation was gauged by the expression levels of macrophage scavenger receptor A (SR-A), a macrophage marker. At day 10 in culture, macrophages (n=4) expressed mRNAs for multiple Notch receptors and ligands (mean PCR $C_T$: Notch1, 30.77; Notch2, 26.89; Notch3, 28.45; Notch4, 33.91; Dll1, 34.79; Dll3, 36.45; Dll4, 40.00; Jagged 1, 28.38; Jagged 2, 35.75). Notably, expression levels of Dll4 were lower than those of other Notch ligands. Macrophages also expressed ADAMs that participate in receptor cleavage, and Fringe proteins that modulate ligand-mediated signaling (mean PCR $C_T$: ADAM10, 25.31; ADAM17, 28.43; Lunatic Fringe, 33.87; Manic Fringe, 27.62; Radical Fringe, 26.59). Differentiation was accompanied by a marked rise in Notch3 mRNA, which increased 10.1±5.0 fold and 16.4±11.4 fold by days 7 and 10, respectively (both P<0.05). In contrast, Notch1 and Notch4 mRNA expression was reduced at days 7 and 10 (both P<0.05), whereas Notch2 expression was unchanged. Jagged2, Manic Fringe, and Radical Fringe also increased during macrophage differentiation. Western blots showed increased expression of full-length Notch3 protein at day 10, corroborating the mRNA findings. Relative to their intrinsic GAPDH expression, human primary macrophages expressed more Notch3 mRNA than human aortic SMC and radial artery EC (both P<0.05 vs. macrophages).

Proinflammatory Stimuli Induces Dll4 Expression in Human Macrophages

We used LPS (Ultra-pure LPS, InvivoGen) to broadly ascertain the effects of a proinflammatory stimulus on the Notch pathway in human primary macrophages. LPS stimulation (100 ng/ml) for 3 h led to a dramatic induction of Dll4 mRNA in 24 different macrophage donors (3,776.3±1717.1 fold increase, P=3.08×10$^{-7}$). One donor among four represents Dll4 expression triggered by LPS in a time- and dose-dependent manner. The expression of Notch receptors did not change substantially with LPS treatment. LPS increased mRNA levels of Jagged1 (6.1±1.2 fold, P<0.01) and ADAM17 (3.0±0.7 fold, P<0.05, n=5).

We also examined the effects of other proinflammatory stimuli that are implicated in atherogenesis. mmLDL and IL-1 beta increased Dll4 mRNA expression (68.7±36.3 fold and 130.9±61.7 fold, respectively, at 3 h, both P<0.01) in macrophages, whereas tumor necrosis factor alpha (TNF-alpha), interferon gamma (IFN-gamma) and granulocyte macrophage-colony stimulating factor (GM-CSF) had no significant effect.

Western blot analysis showed that LPS and IL-1beta also increased expression of Dll4 protein. Furthermore, although the mRNA and protein levels of Notch3 were not increased, in Western blots stained with an antibody specific for the intracellular domain of Notch3, we observed that LPS induced a shift in the Notch3 polypeptides from 280 kD (the size of newly synthesized, unprocessed Notch3) to 100 kD (the size of furin-processed Notch3). These findings suggest that LPS increases the furin-processing of Notch3, an event that is predicted to enhance both the surface expression of Notch3 and therefore its availability to ligand.

TLR4 Silencing and NF-kappaB Inhibition Limits Dll4 Induction by LPS

TLR4 serves as a receptor for LPS. TLR4 siRNA treatment silenced TLR4 mRNA expression in human macrophages (P<0.05 vs. control siRNA), and decreased LPS-induced Dll4 mRNA expression (P<0.05 vs. LPS+control siRNA). To examine the possible role of the NF-kappaB pathway downstream of TLR4 in LPS-induced Dll4 expression, we used a cell-permeable peptide, SN50 (Calbiochem), that inhibits nuclear translocation of the active NF-kappaB complex containing the p50 subunit. SN50 substantially reduced Dll4 expression at 100 µg/ml (95.8±3.3%; P<0.05 vs. LPS only group), whereas SN50M, the control peptide, did not affect Dll4 expression.

Dll4 Binding to Macrophages Triggers Notch Signaling

To examine whether Dll4 binds to macrophages and triggers Notch signaling, we performed four assays. First, we detected significant binding of the Dll4.Fc-biotinylated IgG complex to human macrophages as compared to the control Fc-biotinylated IgG complex or streptavidin-PE alone. Other experiments were conducted with feeder cell lines stably transfected with a vector expressing GFP alone (MS5-GFP) or Dll4-GFP (MS5-Dll4); these feeder cells are much less adherent to culture dishes than are macrophages, making it possible to remove these cells prior to harvesting of macrophages for analysis. Human primary macrophages co-cultured with MS5-Dll4 generated Notch1$^{ICD}$, the activated form of Notch1. The accumulation of Notch1$^{ICD}$ was sensitive to compound E, a potent gamma-secretase inhibitor, suggesting that Dll4 activates the canonical Notch signaling pathway. Third, the Dll4.Fc-IgG complex, but not Fc-IgG, also induced Notch1$^{ICD}$ production. Fourth, when co-cultured with MS5-Dll4 cells, the RAW264.7 macrophage cell line showed a >10-fold increase in the activity of a Notch-sensitive luciferase reporter gene that contains multiple binding sites for RBP-Jkappa/CBF-1, the key transcription factor that acts downstream of Notch.

Dll4-Notch Binding Induces Inflammatory Pathways and Genes in Macrophages

Of further interest, Dll4 binding increased phosphorylated extracellular signal-regulated kinases 1 and 2 (ERK1/ERK2) and Akt in human primary macrophages, indicating that Notch signaling induces mitogen-activated protein kinase (MAPK) and Akt pathways in this cell type. Co-culture with MS5-Dll4 also decreased IkappaBalpha accumulation in human primary macrophages, indicative of activation of the NF-kappaB pathway. Furthermore, Dll4-activated Notch signaling augmented inflammation-associated molecules including iNOS (n=12, $p<0.01$), PTX3 (n=12, $p<0.01$), and Id1 (n=5, $p<0.01$) in day 10 macrophages. siRNA targeting each of the four Notch receptors led to partial reduction of Dll4-induced increase of iNOS, PTX3 and Id1, suggesting functional signaling of Dll4 through all four Notch receptors. Additionally, Notch3 siRNA applied to day 5 differentiating macrophages led to diminished expression of iNOS, PTX3, Id1 and SR-A at day 10 when macrophages become differentiated. Dll4 binding further promoted macrophage expression of Dll4 (n=4, $p<0.01$), suggesting the positive Dll4-Notch feedback loop.

Dll4 Colocalizes with Macrophages in Human Atherosclerotic Plaques

Immunohistochemical staining for Dll4 and other Notch components, including Notch3, colocalized with immunoreactive CD68, a macrophage marker, in the tunica intima of human atherosclerotic plaques. Neither nonimmune IgG nor PBS showed positive staining. Computer-assisted color image quantification followed by statistical regression analysis demonstrated that immunoreactivity for Dll4 correlated positively with CD68 staining. Although immunostaining did not demonstrate clearly whether subpopulations of macrophages express Dll4, Notch3, or both, there was a strong statistically significant correlation between Dll4 and Notch3 staining. Staining for other ligands—Dll1, Jagged1, and Jagged2—also correlated positively with CD68 staining. Taken together, these data suggest that atherosclerotic plaques rich in macrophages contain greater amounts of Notch components.

C. Discussion

The present study affirms our hypothesis that the Notch pathway plays an important role in macrophages, a key cell type in inflammation and atherosclerosis. Evidence supporting this idea includes: 1) the expression of multiple Notch receptors and ligands in human macrophages; 2) markedly enhanced Dll4 expression in human macrophages stimulated with LPS, mmLDL, or IL-1beta, an event that likely involves TLR4 and NF-kappaB; 3) the ability of Dll4 to bind to macrophages and trigger Notch signaling; 4) Dll4-triggered activation of the MAPK, Akt, and NF-kappaB pathways in macrophages; 5) augmentation of gene transcription of iNOS, PTX3, Id1, and Dll4 through Dll4-induced Notch signaling; and 6) increased expression of Notch pathway components including Dll4 and Notch3 in human atherosclerotic plaques rich in macrophages. Taken together, our results concur with the hypothesis that Notch signaling participates in juxtacrine homotypic communication between macrophages and also in amplification of the proinflammatory milieu in inflamed tissues.

Example 2

Notch Signaling Induces Macrophage Gene Expression Associated with Inflammation and Atherosclerosis The present example presents results that demonstrate that Notch signaling regulates the induction of various proinflammatory genes, suggesting that this pathway participates in macrophage activation and the pathogenesis of inflammatory diseases including atherosclerosis.

A. Methods

Cell Culture

RAW 264.7 cells were from American Type Culture Collection (ATCC), and were grown at 37° C. under 5% CO2 in Dulbecco's modified Eagle's medium (DMEM, Gibco) supplemented with 10% fetal bovine serum (BioWhittaker), 4 mM L-glutamine, 50 U of penicillin G/ml, and 50 mg of streptomycin/ml.

Plasmid Construction and Purification

Plasmid DNA constructs encoding FLAG-tagged intracellular domains of mouse Notch1 (N1ICD), Notch2 (N2ICD), Notch3 (N3ICD), the dominant negative mastermind-like protein 1 (DNMAML1) and eGFP were amplified in chemically competent *E. coli*, purified using EndoFree Plasmid Kits (Qiagen), and resuspended in endotoxin free TE buffer with a concentration at 1.0 mg/ml for transfection.

Plasmid DNA Transfection

The cells were subcultured in a 150 cm$^2$ flask, three days before the transfection studies to reach about 80-90% confluency. Plasmid transfection employed electroporation. In each reaction, $4.0 \times 10^6$ RAW 264.7 cells were electroporated with plasmid DNA. The protein expression of N3ICD was confirmed by immunoblotting using anti-FLAG antibody (Sigma, St. Louis, Mo.). We also confirmed the N3ICD expression within 48 h after the transfection by following up the time course of mRNA expression by real-time PCR.

Luciferase Assay

We collected transfected cells 48 h after transfection and measured luciferase activity in a Berthold luminometer (Lumat LB9501, Berthold Technology) using the dual luciferase reporter assay system (Dual-Luciferase Reporter Assay System, Promega). The efficiency of transcription was measured and normalized in relation to the activity of pRL-SV40 *Renilla* (Promega), and the activity reported as the ratio of firefly/*Renilla* luciferase activity according to the manufacture's instruction.

DNA Microarray Analysis

We employed a high-throughput DNA microarray (Affymetrix GeneChip Mouse Genome 430A 2.0 Array (Affymetrix) representing approximately 14,000 well-characterized mouse genes) on total RNA samples obtained from N3ICD-transfected (n=3) or vehicle-transfected (n=3) RAW 264.7 cells at the GeneChip Microarray Facility of Harvard Medical School-Partners Healthcare Center for Genetics and Genomics. In each reaction, $4.0 \times 10^6$ RAW 264.7 cells were transfected with 5.0 mg plasmid DNA. Total RNA was isolated from the each well 48 h after transfection using RNeasy kit (Qiagen). DNase digestion with RNase-free DNaseI (Qiagen) was performed during RNA purification. Primary data were processed using GeneCluster 2.0 software (Whitehead/MIT Center for Genome Research) to determine the average difference value and assess signal intensity for each probe set. We further performed clustering analysis using GeneSifter.

Immunoblotting and ELISA for Interleukin-1beta

Cells were lysed in extraction buffer (20 mM Tris, 100 mM NaCl, 1% Triton X-100, 50 mg of NaF/ml, 1 mM Na3VO4, 0.2 mM phenylmethylsulfonyl fluoride, 10 mg of aprotinin/ml, and 10 mg of leupeptin/ml) 48 h after transfection. Protein concentration was determined for each sample using the BCA protein assay system (Pierce). Lysate samples containing same amount (100-200 mg) of protein were electrophoresed on 10% SDS-polyacrylamide gel, transferred to PVDF membranes, and reacted with anti-IL-1beta antibody (Santa Cruz Biotechnology). Blots were then reacted with a goat anti-rabbit IgG peroxidase-linked conjugate secondary antibody (Amersham, Arlington Heights, Ill.), and proteins were detected by chemiluminescence system (Western Lightning, PerkinElmer). We quantified IL-1beta protein production using ELISA system (eBioscience).

Real Time Quantitative PCR

After reverse transcription (RT) with total RNA from each reaction, real-time PCR was carried out using iQ™ SYBR Green Supermix (Bio-Rad, Hercules, Calif.) on MyiQ™ Single-Color Real-Time PCR Detection System (Bio-Rad). Final primer concentration was 300 nM each, and DNA content in each reaction was ideally 20 ng. To determine the relative expression levels of each transcript, we employed the comparative $C_T$ (fractional cycle number for which the amount of amplified target reaches a fixed threshold) method using GAPDH as a reference gene for normalization of each value owing to its stability in the experiment.

IL-1Beta Promoter Assay

Reporter plasmids contained various lengths of the mouse IL-1beta promoter region: IL-1beta 5'-flanking sequence (4093 bp and 50 bp from the transcription start site; −4093+I CAT and −50+I CAT) and extended to the 5' portion of the second exon, terminating immediately upstream of the translation initiation codon, followed by the chloramphenicol acetyltransferase (CAT) gene and simian virus 40 splice and polyadenylation sites. The first intron is necessary for optimal CAT expression as previously described (Godambe, et al., Mol. Cell. Biol. 15(1):112-119 (1995)). The same copy amount of each CAT plasmid (equal to 2.5 mg of −4093+I CAT) was cotransfected with 2.5 mg of N3ICD in $4.0\times10^6$ RAW 264.7 cells. The IL-1beta promoter activity was determined 48 h after transfection using CAT ELISA (Roche) as instructed.

Transfection of siRNA Oligos for RBP-Jκ in Human Primary Macrophages

Human monocytes were isolated from human peripheral blood by density gradient centrifugation and adherence, then plated at $5\times10^6$ cells/well on plastic plates in RPMI 1640 medium containing 5% human serum and cultured for 14 days until they are fully differentiated to macrophages. We transfected siRNA oligos of human RBP-Jkappa (siGENOME™ SMARTpool siRNA, Dharmacon) in human macrophages to abolish RBP-Jkappa expression using the transfection reagent Lipofectamine™ 2000 (Invitrogen) as instructed. The final siRNA transfection medium contained 3 nM of siRNA oligos and 4 ul of Lipofectamine™ 2000 reagent in Opti-MEM (Gibco). Twenty-four hours after starting transfection, the transfection medium was completely replaced by the culture medium containing human serum again. We confirmed the inhibition of RBP-Jkappa expression in macrophage by real time PCR and Western blot 72 h after the medium exchange.

B. Results

RBP-Jkappa-Mediated Transcriptional Activation by N3ICD in Macrophages

We verified the expression of N3ICD using anti-FLAG antibody. Western blots showed the accumulation of N3ICD in the nucleus. We also confirmed the expression of Notch component genes including RBP-Jkappa and MAML1 in RAW 264.7 cells by RT-PCR. To examine whether N3ICD drives RBP-Jkappa-mediated transcriptional activation, we cotransfected N3ICD or vehicle plasmid (3.0 mg), CBF1-luc (1.0 mg), and pRL-SV40 (0.5 mg, an internal control) in $4.0\times10^6$ RAW cells as described. 48 h after the transfection, N3ICD significantly induced RBP-Jkappa-mediated transcription detected by the increase in luciferase activity indicating that NICD activates Notch signaling in macrophages.

Exploring Target Genes of Notch Signaling; Microarray Analysis and Real-Time PCR DNA microarray analysis revealed that Notch signaling increased or decreased a wide variety of genes in macrophages. We used N3ICD because our recent data indicated that Notch3 mRNA expression increased in human primary macrophages during differentiation, suggesting a potential role of Notch3 in macrophage biology. We calculated the fold difference in each probe set between the N3ICD-transfected and vehicle-transfected samples (n=3 each). Scatter plots showed the overall distribution of the genes arrayed on the chip. The core pathway of Notch signaling is mediated by RBP-Jkappa in association with other co-activators including MAML1 that functions as a transcriptional activator. This study primarily focused on the increased genes to explore the target genes under the regulation of Notch signaling. We categorized the increased genes according to the biological process in reference to Human Protein Reference Database (Peri, et al., Genome Res. 13(10):2363-2371 (2003)). Notably, the genes involved in the immune response most remarkably increased. Some pro-inflammatory genes including IL-1kappa ranked among the most increased genes. Real-time PCR validated fold increases of mRNA expression of pro-inflammatory genes showing more than a four-fold increase on the DNA array [complement component 1 q subcomponent a, b and g (C1qa, C1qb, C1qg), IL-1beta, IL-1alpha, SAA3, CXCR4, MMP-9, and integrin-aL]. Fold increases obtained from the DNA microarray data correlated well to those of real-time PCR. On the other hand, according to the results of DNA microarray analysis and real-time PCR, N3ICD expression did not affect the mRNA expression of other pro-inflammatory genes such as TNF-alpha, IFN-gamma, and tissue factor, indicating the selective transcriptional regulation by Notch signaling. Examples of other increased genes, which may contribute to the macrophage-mediated inflammation, include MMP-8 (3.9 fold), CD97 (3.6 fold), platelet derived growth factor receptor beta (3.4 fold), IL-4 receptor (3.4 fold), histocompatibility 2, class II antigen A beta1 (3.3 fold), monocyte chemoattractant protein (MCP)-5 (3.1 fold), VLDL receptor (3.0 fold), MMP-3 (2.8 fold), CD27 (2.7 fold), syndecan-1 (2.6 fold), MMP-14 (2.4 fold), IL-7 receptor (2.4 fold), toll-like receptor 1 (2.3 fold), MCP-1 (2.3 fold), macrophage scavenger receptor type 1 (2.3 fold), insulin-like growth factor 1 receptor (2.2 fold), insulin-like growth factor 1 (2.1 fold), angiotensin II receptor, type 1 (2.1 fold), cathepsin H (2.1 fold), CD86 (2.1 fold). Jagged 1 (2.7 fold) and Delta-like 3 (2.6 fold), the Notch ligands, also increased.

NICD Induced IL-1 β Expression in Murine Macrophages

We transfected various amounts of the N3ICD plasmid in RAW 264.7 cells (1.0, 3.0, and 5.0 mg plasmid DNA in $4.0\times10^6$ cells, respectively). N3ICD increased IL-1beta mRNA expression strikingly in a concentration-dependent manner, supporting the DNA microarray data. N1ICD and N2ICD also increased IL-1beta mRNA expression. Western blotting revealed a remarkable increase of the IL-1beta protein (pro-form; 31 kDa) 48 h after transfection. ELISA further quantified the IL-1beta protein production (in the whole cell lysate) and secretion (in the culture medium) induced by N3ICD. The magnitude of IL-1beta protein induction correlated well with that of mRNA levels. We further evaluated the promoter activity of mouse IL-1beta in RAW 264.7 cells using a CAT ELISA. N3ICD substantially increased the promoter activity and deletion of the 5' upstream (−50+I CAT) abolished the N3ICD-induced activity.

DNMAML-1 Inhibited NICD-Induced IL-1 Beta Expression

To determine whether the IL-1β induction involves the Notch-RBP-Jkappa mediated core pathway, we cotransfected DNMAML-1 (2.5 mg) and N3ICD (2.5 mg) in addition to RBP-Jkappa-luc (1.0 mg) and pRL-SV40 (0.5 mg) vectors in RAW 264.7 cells. Transfection of DNMAML-1 (2.5 mg) and N3ICD (2.5 mg) plasmids in $4.0 \times 10^6$ cells almost completely abolished the increase in IL-1beta mRNA expression 48 h after transfection. DNMAML1 recruits NICD and binds to RBP-Jkappa, then antagonizes the binding of other essential cofactors such as CBP/p300. Hence, it is assumed that the ternary complex composed of NICD, DNMAML-1, and RBP-Jkappa does not function as a transcriptional activator. DNMAML-1 also abolished IL-1beta induction by N1ICD and N2ICD in the same manner. These results indicate the IL-1beta induction by NICD depends on the RBP-Jkappa and MAML1-mediated pathway.

Notch-Mediated Increases of Various Proinflammatory Genes

We also validated dose-dependent increases of various increased genes [C1qa, C1qb, C1qg, IL-1alpha, IL-10, H2-IEa, CXCR4, CD97, Integrin-alpha L, Aif-1, and Nuclear receptor subfamily 1, group H, member 3 (Nr1h3)] by N3ICD in RAW 264.7 cells by transfection various amounts of the N3ICD plasmid in RAW 264.7 cells (1.0, 3.0, and 5.0 mg plasmid DNA in $4.0 \times 10^6$ cells, respectively). N1ICD and N2ICD (5.0 mg plasmid DNA in $4.0 \times 10^6$ cells) also increased these genes in the same manner. DNMAML1 abolished the increases of these genes in the same manner as of IL-1beta indicating the specific regulation of these increased genes by Notch signaling.

Induction of IL-1beta mRNA in Human Primary Macrophages

To determine whether Notch signaling induces IL-1beta expression in human macrophages, we performed co-culture experiments using MS5-Dll4 cells and human primary macrophages derived from peripheral blood monocytes. Dll4 binding increased IL-1beta mRNA expression in human macrophages determined by real-time RT-PCR (6 h, 98.2 fold, n=10, $p<0.01$).

C. Discussion

This study explored the mechanism of macrophage activation through Notch signaling, and demonstrates that Notch signaling may regulate various pro-inflammatory genes, including IL-1beta, a novel target gene of this signaling pathway in any cell type. The results suggest a role of Notch signaling in inflammation and atherosclerosis through macrophage activation. In addition, the results of DNA microarray analysis, suggest that Notch signaling may regulate, directly and indirectly, various genes associated with inflammation over various functional categories, including the immune response (e.g., C1q, IL-1beta, IL-1alpha), signal transduction (e.g., Nr1h3, CXCR4, allograft inflammatory factor1), transport (e.g., serum amyloid A3), protein metabolism (e.g., MMP-9), cell growth and/or maintenance (e.g., myristoylated alanine rich protein kinase C).

All references cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. A method of treating a patient for atherosclerosis, comprising:
   a) assaying a biopsy sample from said patient for the amount or activity of NOTCH-3 receptor or Delta-like 4 (Dll4) and said amount or activity is elevated relative to one or more controls, and wherein said biopsy sample is cells or fluid derived directly from an atherosclerotic plaque; and
   b) administering systemically or locally to said patient a therapeutically effective amount of a compound that inhibits the binding of a ligand to the NOTCH-3 receptor, wherein said compound is not an RNA interfering agent or plasmid DNA.

2. The method of claim 1, wherein said compound is administered orally as a capsule, tablet or pill.

3. The method of claim 1, wherein said compound is administered systemically by injection.

4. The method of claim 1, wherein said compound is administered locally by injection.

5. The method of claim 1, wherein said compound is a blocking antibody.

6. The method of claim 1, wherein said ligand is selected from the group consisting of: Delta-like 4 (Dll4); Delta-like 3 (Dll3); Delta-like 1 (Dll1); Jagged 1; and Jagged 2.

7. The method of claim 1, wherein said compound also inhibits the binding of a ligand to one or more receptors selected from the group consisting of: a NOTCH-1 receptor; a NOTCH-2 receptor; and a NOTCH-4 receptor.

8. The method of claim 7, wherein said compound is administered orally as a capsule, tablet or pill.

9. The method of claim 7, wherein said compound is administered systemically by injection.

10. The method of claim 7, wherein said compound is administered locally by injection.

11. The method of claim 7, wherein said compound is a blocking antibody.

12. The method of claim 11, wherein said ligand is selected from the group consisting of: Delta-like 4 (Dll4); Delta-like 3 (Dll3); Delta-like 1 (Dll1); Jagged 1; and Jagged 2.

13. The method of claim 1, further comprising treating said patient with an additional compound that inhibits the binding of a ligand to one or more receptors selected from the group consisting of: a NOTCH-1 receptor; a NOTCH-2 receptor; and a NOTCH-4 receptor, and wherein said additional compound is not an RNA interfering agent or plasmid DNA.

14. The method of claim 13, wherein said compound and said additional compound are administered orally as a capsule, tablet or pill.

15. The method of claim 13, wherein said compound and said additional compound are administered systemically by injection.

16. The method of claim 13, wherein said compound and said additional compound are administered locally by injection.

17. The method of claim 13, wherein said compound and said additional compound are blocking antibodies.

18. The method of claim 17, wherein said ligand is selected from the group consisting of: Delta-like 4 (Dll4); Delta-like 3 (Dll3); Delta-like 1 (Dll1); Jagged 1; and Jagged 2.

* * * * *